United States Patent
Prenerova et al.

(10) Patent No.: US 8,574,566 B2
(45) Date of Patent: Nov. 5, 2013

(54) **STRAIN OF ENTOMOPATHOGENIC FUNGUS *ISARIA FUMOSOROSEA* CCM 8367 (CCEFO.011.PFR) AND THE METHOD FOR CONTROLLING INSECT AND MITE PESTS**

(75) Inventors: Eva Prenerova, Bernartice u Milevska (CZ); Rostislav Zemek, Stare Hodejovice (CZ); Lubomir Volter, Plzen (CZ); Frantisek Weyda, Ceske Budejovice (CZ)

(73) Assignees: Biology Centre AS CR, V.V.I., Ceske Budejovice (CZ); Eva Prenerova, Bernartice u Milevska (CZ)

( * ) Notice: Subject to any disclaimer, the term of this patent is extended or adjusted under 35 U.S.C. 154(b) by 260 days.

(21) Appl. No.: 13/000,562

(22) PCT Filed: Jun. 23, 2009

(86) PCT No.: PCT/CZ2009/000088
§ 371 (c)(1),
(2), (4) Date: Jan. 14, 2011

(87) PCT Pub. No.: WO2010/006563
PCT Pub. Date: Jan. 21, 2010

(65) Prior Publication Data
US 2011/0110895 A1    May 12, 2011

(30) Foreign Application Priority Data
Jun. 23, 2008  (CZ) .................................... 2008-394

(51) Int. Cl.
*A01N 63/00*  (2006.01)
(52) U.S. Cl.
USPC ........................................ 424/93.5; 435/254.1
(58) Field of Classification Search
None
See application file for complete search history.

(56) References Cited

U.S. PATENT DOCUMENTS 5,360,607 A  *  11/1994  Eyal et al. .................... 424/93.5

OTHER PUBLICATIONS

Osborne et al., "Potential of entomopathogenic fungus *Isaria fumosorosea* to protect potted ornamental plants against *Bemisia tabaci* during shipping", International Organization for Biological Control/WPRS, 2008, Bulletin, 32. p. 159-165, Summary.*
Zemek et al., Comm. Appl. Biol. Sci, 2007, vol. 72, No. 3, p. 521-526.*

* cited by examiner

*Primary Examiner* — Kade Ariani
(74) *Attorney, Agent, or Firm* — Notaro, Michalos & Zaccaria P.C.

(57) ABSTRACT

Strain of entomopathogenic fungus *Isaria fumosorosea* CCM 8367 (CCEFO.011.PFR) deposited in collection CCM (Czech Collection of Microorganisms) in Brno, applicable for biological control of substrates infested by insect and mite pests. Infested woods, plants, etc. are treated with blastospores or conidiospores of this strain.

12 Claims, 1 Drawing Sheet

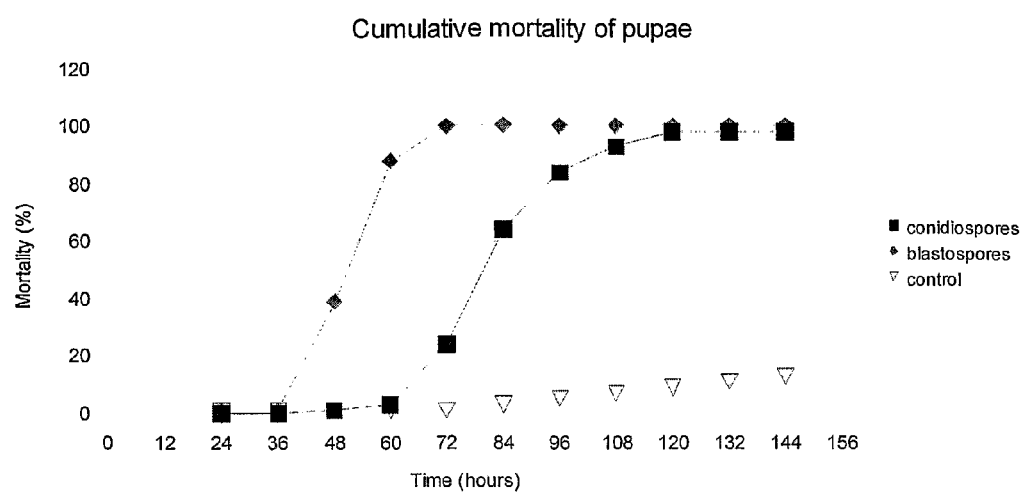

STRAIN OF ENTOMOPATHOGENIC FUNGUS ISARIA FUMOSOROSEA CCM 8367 (CCEFO.011.PFR) AND THE METHOD FOR CONTROLLING INSECT AND MITE PESTS

TECHNICAL FIELD

This application claims the priority benefit of Czech patent application PV 2008-394 (filed Jun. 23, 2008) and PCT application No. PCT/CZ09/00088 (filed Jun. 23, 2009). Mycoinsecticide which is usable as a considerate biological means of plant and wood protection against insect and mite pests.

BACKGROUND ART

Plant protection against insect pests is performed largely using conventional chemical insecticides. Their application is, however, problematic from nature conservation and human health points of view. Insects become more and more resistant to them which in turn leads to the increase of dosage or needs to develop other more effective insecticides. The opportunities in this direction are approaching the limits. More rigorous legislative also restrains this way of pest control.

The horse chestnut leaf miner, *Cameraria ohridella* (Deschka et Dimič) (Lepidoptera: Gracillariidae) has favourable conditions for its development in the Czech Republic. This pest was discovered for the first time at Ohrid lake in Macedonia between Albania and Greece in 1984. This important pest of the horse chestnut started to spread invasively through whole Europe where it has good conditions for its development (for the lack of natural enemies) while not being enough regulated by natural mechanisms. Damage inflicted to horse chestnut leaves cause serious weakening of most of the infested trees. Contemporary pest control methods are based either on the application of non-selective insecticides or composting or burning of decaying (fallen) leaves. All these methods, however, also kill beneficial organisms including natural enemies of *Cameraria ohridella*.

An application of biological control, i.e. methods based on natural antagonistic interactions between organisms for suppression of pest population is safer to natural balance and stability of agricultural and forests ecosystems. Most of these biocontrol agents are harmless for non-target organisms including man and, contrary to chemical insecticides, do not posses any ecological risk for environment and thus contribute to biodiversity conservation. For this reason, biocontrol agents are more and more preferred as alternative means of insect pest control at the global scale.

Mycoinsecticides are such means of biological control. They are based on entomopathogenic fungi. For practical pest control representatives of several key Deuteromycet (Hyphomycetes: Moniliales) are of dominant importance. The best known are entomopathogenic fungi belonging to the genera *Beauveria, Hirsutella, Metarhizium, Nomuraea, Isaria (Paecilomyces), Tolypocladium* and *Verticillium (Lecanicillium)*. Among many species of these genera about 25 species are contemporarily used in the form of standard biopesticides. Application of mycoinsecticides in pest control is one of the approaches in modern applied entomology and their development reached the stage of commercial bioinsecticides in many countries.

Entomopathogenic fungus *Isaria fumosorosea* (syn. *Paecilomyces fumosoroseus*) (WIZE) Brown & Smith is in comparison to other species of entomopathogenic Deuteromycet (*Beauveria bassiana, Metarhizium anisopliae, Verticillium lecanii* etc.) a less studied species. Fungus *Isaria fumosorosea* (syn. *Paecilomyces fumosoroseus*), often reported under abbreviation PFR, is a cosmopolite polyphagous entomopathogenic species. Most records of the isolation of this fungus from insects (under natural conditions) frequently report species of the orders Lepidoptera, Diptera and Coleoptera as the hosts. The PFR was for the first time reported as naturally occurring pathogen in the whitefly (*Trialeurodes vaporariorum*) populations in Peking in 1983, where strong local epizootics occurred, which temporarily eradicated this pest. This strain of PFR was isolated and as highly virulent against greenhouse whitefly was assigned as a subspecies *Paecilomyces fumosoroseus* var. *beijingensis*.

Substantial increase of interest in this pathogen happened when harmfulness of the whitefly *Bemisia tabaci* increased in field agroecosystems in Southern USA. Since 1987 regular spontaneous epizootics of *Paecilomyces fumosoroseus* in *Bemisia tabaci* populations on various host plants/localities were reported in Florida where a new strain of *Paecilomyces fumosoroseus* (PFR) was isolated in 1987. The isolated strain was assigned as PFR 97—strain Apopka (Apopka—name of the region in Florida. The pure culture was identified in 1988 and deposited at the American Type Culture Collection (strain ATCC 20874). Strain PFR 97 turned out to be able to cause large epizootics in *Bemisia tabaci* populations both in greenhouses and in the field crops. Further experiments with this strain proved the polyphagous feature of this strain and a high virulence against aphids, thrips, larvae of certain moth species, larvae and pupae of leafminers (Diptera) and even a high activity against two-spotted spider mite (*Tetranychus urticae*). Contrary to the fungus *Verticillium lecanii*, PFR is able to cause infection also in the eggs of whiteflies and spider mites.

DISCLOSURE OF THE INVENTION

Research and development of new means of plant protection based on influencing physiological processes in a pest organism (so called biorational insecticides, i.e. means based on natural models), or on principles of biological control when natural enemies of pests like predators, parasitoids or pathogenic organisms are used, is a solution for modern plant protection. Biological control methods utilize natural antagonistic interactions between organisms for the suppression of pest population without disturbing natural balance so that they contribute to the stability of ecosystems in man-affected environment. The biocontrol agents proved to be harmless for the non-target organisms including man and, contrary to chemical insecticides, do not posses any ecological risk for the environment and thus contribute to biodiversity conservation. For this reason, biocontrol agents are more and more preferred as alternative means of insect pest control at the global scale. Our strain of entomopathogenic fungus *Isaria fumosorosea* with high virulence is a prospective biocontrol agent against insect and mite pests. The *Isaria fumosorosea* strain is deposited under accession number CCM 8367 (CCEFO.O11.PFR) as patent culture in CCM collection (Czech Collection of Microorganisms). The CCM is located at Masaryk University, Faculty of Science, Tvrdeho 14, 602 00 Brno, Czech Republic, which depository is recognized under the Budapest Treaty. The deposit was received by the CCM on May 16, 2008. The deposit will be irrevocably made available to the public on the granting of a patent including the deposited organism. The organism will be maintained in a viable and uncontaminated state. Spores of this microorganism attack insect pests and mites and kill them.

A preparation based on the spores of *Isaria fumosorosea* strain CCM 8367 for control of insect pests (belonging to the orders Lepidoptera, Coleoptera, Hymenoptera and Homoptera) and mites is made by submerged or surface cultivation. For application, homogenous suspension of spores is prepared from a biomass concentrate or the spores are applied in the mixture with an inert carrier. After the application the fungus grows and infects insect pests and mites which then die. The advantage is that the fungus is a microorganism naturally occurring in the environment, and thus no disturbance of the ecosystem is made.

FIGURE

FIG. 1: Cumulative mortality of *Cameraria ohridella* pupae after the treatment with conidiospores or blastospores of CCM 8367 strain of *Isaria fumosorosea* or with distilled water (control).

EXAMPLES

Example 1

Application of Conidiospores of CCM 8367 Strain of *Isaria fumosorosea* Against Pupae of the Horse Chestnut Leaf Miner Conidiospores were collected from the fungus *Isaria fumosorosea* grown on agar dish (Sabouraud agar) and put into 50 ml of sterile distilled water with 10 µl of the soaking agent Tween. Homogenous suspension prepared by a hand homogenizer was diluted to the concentration of $5 \times 10^7$ conidiospores/ml.

One hundred of hibernating pupae of the horse chestnut leaf miner was collected from fallen leaves of horse chestnut trees. Each pupa was immersed (dipped) into the prepared suspension for one second. 100 pupae immersed to distilled water with Tween only served as a control. Pupae were then placed on filter paper to remove excess suspension or water, put into dishes with high humidity and incubated in dark climatized box at 23° C. Survival of pupae was checked using dissection microscope by mechanical stimulation at 12-hours intervals. Resulting mortality of pupae treated by conidiospores or water only is shown in FIG. 1.

Example 2

Application of Blastospores of CCM 8367 Strain of *Isaria fumosorosea* against Pupae of the Horse Chestnut Leaf Miner The strain of *Isaria fumosorosea* was cultivated using orbital shaker at 140 cycles per minute and temperature 23° C. using grow media of the following composition: 2% glucose, 2% maltose, 2% peptone for bacteriology, pH=5.5. The cultivation was stopped after 120 hours and the biomass of blastospores was isolated from the grow media by centrifugation at 2500 rotations/min. for 20 minutes. A suspension of blastospores was prepared from the biomass by diluting with distilled water so that the concentration was $5 \times 10^7$ blastospores/ml. One hundred of hibernating pupae of the horse chestnut leaf miner was collected from fallen leaves of the horse chestnut trees. Each pupa was immersed into the prepared suspension of blastospores for one second. 100 pupae immersed to distilled water with Tween only served as a negative control. The pupae were then placed on filter paper to remove excess suspension or water, put into dishes with high humidity and incubated in dark climatized box at 23° C. Survival of pupae was checked using dissection microscope by mechanical stimulation at 12-hours intervals. Resulting mortality of pupae treated by blastospores or water only is shown in FIG. 1.

Example 3

Application of Conidiospores of CCM 8367 Strain of *Isaria fumosorosea* Against the Eggs of the Horse Chestnut Leaf Miner Conidiospores were collected from fungus *Isaria fumosorosea* grown on agar dish (Sabouraud agar) and put into 100 ml of sterile distilled water with 20 µl soaking agent Tween. Homogenous suspension prepared by a hand homogenizer was diluted to the concentration of $5 \times 10^7$ conidiospores/ml. A leaf of the horse chestnut tree, *Aesculus hippocastanum*, with deposited eggs of *Cameraria ohridella* (Deschka et Dimič) (Lepidoptera: Gracillariidae) was immersed into the prepared suspension for one second. Another leaf with the eggs immersed into distilled water with Tween only served as a negative control. After removing excess suspension or water the leaves were placed into dishes with high humidity and incubated in a dark climatized box at 23° C. Mortality of the eggs was assessed one week later. Totally, 102 eggs were treated with the fungus, 314 eggs served as a negative control. Results showed that the mortality of eggs treated with the suspension of conidiospores was 52.94%, by 40% higher compared to that of negative control.

Example 4

Application of Blastospores of CCM 8367 Strain of *Isaria fumosorosea* Against the Eggs of the Horse Chestnut Leaf Miner The strain of *Isaria fumosorosea* was cultivated using orbital shaker at 140 cycles per minute and temperature 23° C. using grow media of the following composition: 2% glucose, 2% maltose, 2% peptone for bacteriology, pH=5.5. The cultivation was stopped after 120 hours and the biomass of blastospores was isolated from grow media by centrifugation at 2500 rotations/min. for 20 minutes. A suspension of blastospores was prepared from the biomass by diluting in 100 ml of distilled water with 20 µl of the soaking agent Tween so that the concentration was $5 \times 10^7$ blastospores/ml. A leaf of the horse chestnut tree, *Aesculus hippocastanum*, with deposited eggs of *Cameraria ohridella* (Deschka et Dimič) (Lepidoptera: Gracillariidae) was immersed into prepared suspension for one second. Another leaf with the eggs immersed into distilled water with Tween only served as a negative control. After removing excess suspension or water the leaves were placed into dishes with high humidity and incubated in dark climatized box at 23° C. Mortality of the eggs was assessed one week later. Totally, 143 eggs were treated with the fungus, 314 served as a negative control. Results showed that the mortality of eggs treated with the suspension of blastospores was 88.81%, by 76% higher compared to that of negative control.

INDUSTRIAL APPLICABILITY

Biological protection of plants, woods and other organic substrates against insect and mite pests.

The invention claimed is:
1. An isolated and biologically pure culture of a strain of the entomopathogenic fungus *Isaria fumosorosea* CCM 8367

(CCEFO.011.PFR) deposited in the collection CCM (Czech Collection of Microorganisms) in Brno, Czech Republic.

2. A method for controlling insect and mite pests, the method comprising treating a plant or leaf with spores of isolated entomopathogenic fungus *Isaria fumosorosea* CCM 8367 (CCEFO.O11.PFR) deposited in the collection CCM (Czech Collection of Microorganisms) in Brno, Czech Republic.

3. The method for controlling insect and mite pests according to claim 2, wherein the spores are in an inert carrier.

4. The method of claim 2, wherein the pests being controlled are the Horse Chestnut Leaf Miner.

5. The method of claim 2, wherein the pests being controlled are insects of the order Lepidoptera.

6. The method of claim 2, wherein the pests being controlled are insects of the order Coleoptera.

7. The method of claim 2, wherein the pests being controlled are insects of the order Hymenoptera.

8. The method of claim 2, wherein the pests being controlled are mites.

9. A biocontrol preparation comprising isolated entomopathogenic fungus *Isaria fumosorosea* CCM 8367 (CCEFO.011.PFR).

10. The biocontrol preparation of claim 9 comprising blastospores of fungus *Isaria fumosorosea* CCM 8367.

11. The biocontrol preparation of claim 9 comprising conidiospores of fungus *Isaria fumosorosea* CCM 8367.

12. The method of claim 2, wherein the pests being controlled are insects of the order Homoptera.

\* \* \* \* \*